US00PP28556P2

(12) United States Plant Patent
Ault

(10) Patent No.: US PP28,556 P2
(45) Date of Patent: Oct. 24, 2017

(54) ***VERNONIA* PLANT NAMED 'SUMMER'S SWAN SONG'**

(50) Latin Name: ***Vernonia* hybrid**
Varietal Denomination: Summer's Swan Song

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 26 days.

(21) Appl. No.: 14/998,973

(22) Filed: Mar. 10, 2016

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — June Hwu
(74) *Attorney, Agent, or Firm* — Penny J. Aguirre

(57) ABSTRACT

A new cultivar of *Vernonia* plant, 'Summer's Swan Song', that is characterized by its compact, bushy habit with stems that do not lodge, its inflorescence branches that are longer than other *Vernonia* varieties forming an interlocking network of branches that add to the overall plant sturdiness and resistance to stem lodging, its foliage and stems that are tinted red and purple in color, its high resistance to rust and powdery mildew, in being reliably hardy in U.S.D.A. Zones 4 to 9 and in being very drought tolerant.

2 Drawing Sheets

Botanical classification: *Vernonia* hybrid.
Variety denomination: 'Summer's Swan Song'.

BACKGROUND OF THE INVENTION

The present invention relates to a new and distinct cultivar of *Vernonia* plant of hybrid origin and will be referred to hereinafter by its cultivar name, 'Summer's Swan Song'. The new cultivar of *Vernonia* is a hardy herbaceous perennial grown for landscape use.

The new invention arose from an ongoing breeding program by the Inventor in Glencoe, Ill. The objectives of the breeding program are to develop improved cultivars of interspecific hybrids of *Vernonia* with novel ornamental traits such as overall plant height, disease resistance, hardiness in U.S.D.A. Zone 5 and in ground cultural adaptability.

'Summer's Swan Song' was derived from a cross made under controlled conditions in September of 2010 between unnamed unpatented plants of *Vernonia lettermannii* as the female seed parent and *Vernonia angustifolia* 'Plum Peachy' (not patented) as the male pollen parent. 'Summer's Swan Song' was selected in September of 2012 as a single unique plant amongst the resulting seedlings.

Asexual propagation of the new cultivar was first accomplished by shoot tip cuttings by the Inventor in June 2013 in Glencoe, Ill. Asexual propagation by shoot tip cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Summer's Swan Song' as a new and unique cultivar of *Vernonia*.

1. 'Summer's Swan Song' exhibits a compact, bushy habit with stems that do not lodge.

2. 'Summer's Swan Song' exhibits inflorescence branches that are longer than other *Vernonia* varieties forming an interlocking network of branches that add to the overall plant sturdiness and resistance to stem lodging.
3. 'Summer's Swan Song' exhibits foliage and stems that are tinted red and purple in color.
4. 'Summer's Swan Song' exhibits high resistance to rust and powdery mildew.
5. 'Summer's Swan Song' is reliably hardy in U.S.D.A. Zones 4 to 9.
6. 'Summer's Swan Song' is very drought tolerant.

The female parent, an unnamed plant of *Vernonia lettermannii*, differs from 'Summer's Swan Song' in having stems and foliage that are green in color, in having inflorescences that are smaller in size, in having fewer florets per capitulum and in having leaves that are smaller in size with entire margins. The male parent, 'Plum Peachy', differs from 'Summer's Swan Song' in having a plant habit that is taller in size, in having inflorescences that are larger in size, in having leaves that are larger in size and in having more florets per capitulum. 'Summer's Swan Song' can also be compared to the cultivar *Vernonia lettermannii* 'Iron Butterfly' (not patented) and *Vernonia* 'Southern Cross' (not patented). 'Iron Butterfly' is similar to 'Summer's Swan Song' in having a low and dense plant habit and in having a high resistance to powdery mildew and rust. 'Iron Butterfly' differs from 'Summer's Swan Song' in having fewer florets per capitulum, in having leaf margins that are entire, in having foliage that is medium green in color and in having a smaller plant habit. 'Southern Cross' is similar to 'Summer's Swan Song' in having a uniform plant habit with flat to slightly domed tops and in having the same resistance to lodging. 'Southern Cross' differs from 'Summer's Swan Song' in having a plant habit that is taller and wider in shape, in having leaves that are larger in size, in being susceptible to rust and in having foliage that is medium-dark green in color.

BRIEF DESCRIPTION OF THE DRAWINGS

The accompanying colored photographs illustrate the overall appearance and distinct characteristics of the new *Vernonia*. The photographs were taken of 'Summer's Swan Song' as grown in a trial garden in Glencoe, Ill.

The photograph in FIG. 1 provides a top view of a 3 year-old plant of 'Summer's Swan Song' in bloom.

Figure 1:
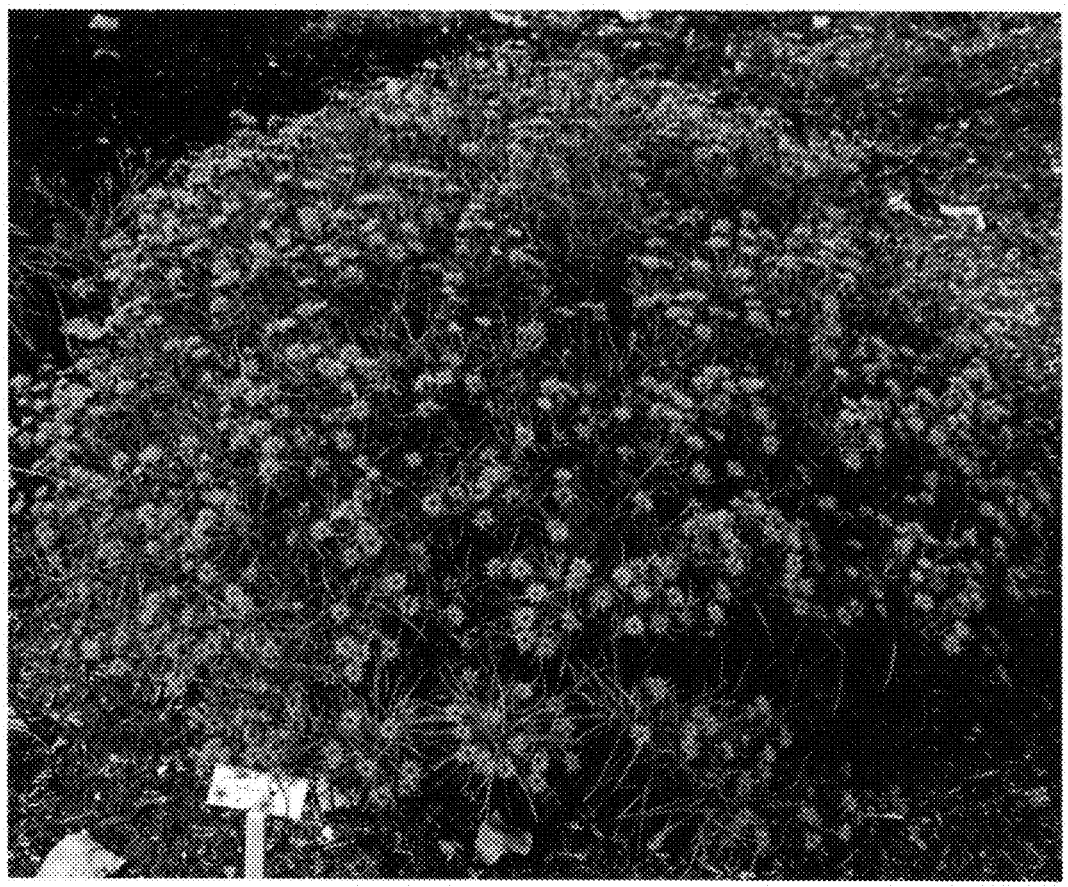
Figure 2:
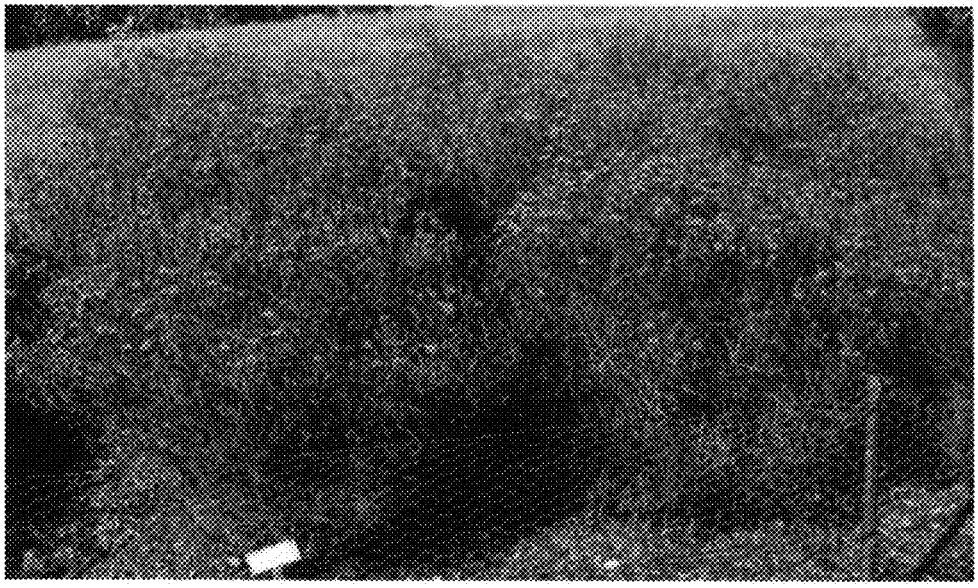

The photograph in FIG. 2 provides a view of the foliage and flowers of a 3 year-old plant of 'Summer's Swan Song'.

Figure 3:
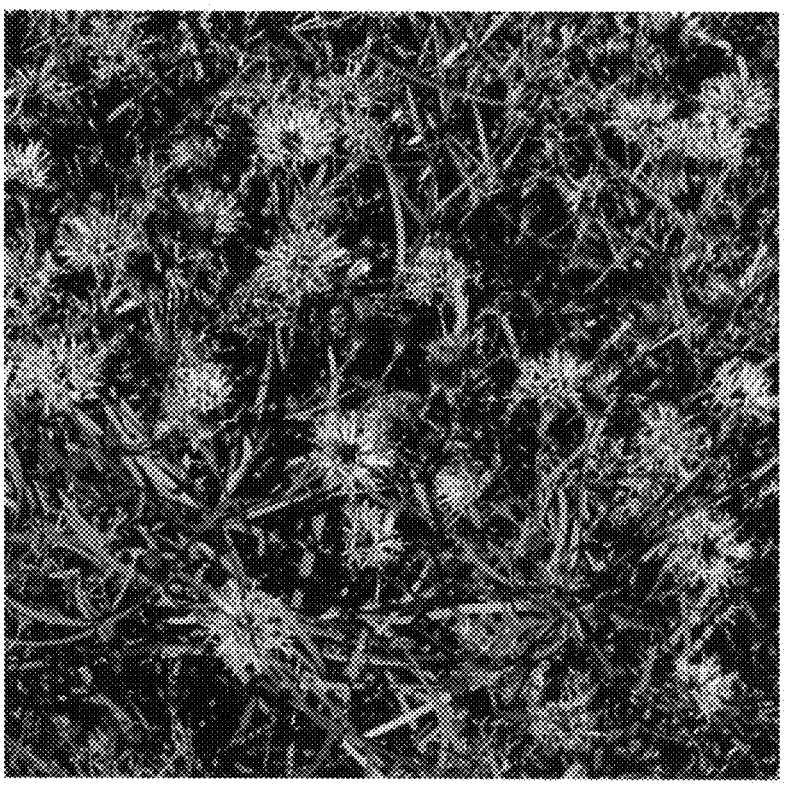

The photograph in FIG. 3 provides a close up view of the flowers of a 4 year-old plant of 'Summer's Swan Song'.

The colors in the photographs are as close as possible with the photographic and printing technology utilized and the color values cited in the Detailed Botanical Description accurately describe the colors of the new *Vernonia*.

DETAILED BOTANICAL DESCRIPTION

The following is a detailed description of five year-old plants of the new cultivar as grown outdoors in a trial plot in Glencoe, Ill. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—An average of 5 to 6 weeks from early September to mid-October in northern Illinois.

*Plant type.*—Herbaceous Perennial.

*Plant habit.*—Compact, bushy habit with stems that do not lodge.

*Height and spread.*—In-ground trial plants 3 years in age; 72 cm in height and 90 cm in width at peak bloom, in-ground trial plants 5 years in age; 78 cm in height and 110 cm in width at peak bloom.

*Hardiness.*—At least hardy in U.S.D.A. Zones 4 to 9.

*Diseases.*—Highly resistant to powdery mildew and rust.

*Root description.*—Fibrous, 155A in color.

*Propagation.*—Shoot tip cuttings.

*Growth rate.*—Vigorous.

*Root development.*—Shoot tip cuttings will root under mist in four weeks in late spring to early summer, rooted cutting will fully root in a 2.5 inch pot in about two months and when transplanted in fall and overwintered in a 4.5 inch pot, they will bloom the following spring.

Stem description:

*Shape.*—Round.

*Stem color.*—Main branch; a blend of 144A, 144B, 144C and 184A, leaf scars a blend of 200A and 166A, lateral branches; mostly 144B on the lower side of branch, upper side of branch is a blend of 144B and 187A at the base and becomes mostly 187A from the mid to top section.

*Stem size.*—Main branches; average of 74.5 cm in length and an average of 5 mm in diameter, lateral branches; average of 15 cm in length and an average of 2 mm in width

*Stem surface.*—Glossy, smooth and ridged, leaf scars are present and an average of 3 scars per linear cm.

*Branching number.*—Average of 65 main branches, an average of 23 branches per main branch.

*Branching habit.*—Main branches occur from the base held at straight upright vertical angle, lateral branches held at a 60° angle (90°=vertical), very strong.

Foliage description:

*Leaf division.*—Simple.

*Leaf arrangement.*—Alternate.

*Leaf shape.*—Linear.

*Leaf size.*—Up to 11 cm in length and 3 mm in width.

*Leaf number.*—Average of 48 per main branch and 17 per lateral branch.

*Leaf base.*—Acute.

*Leaf apex.*—Acute.

*Leaf margin.*—Entire.

*Leaf venation.*—Pinnate, one main middle vein, upper surface color; bottom is 145B sometimes with an overlay of 184B, then turning into a blend of 146A and 147A from the mid section to the tip, lower surface color; 146A.

*Leaf surface.*—Upper surface dull and glabrous, lower surface slightly glossy and glabrous.

*Internode length.*—Up to 1.5 cm.

*Leaf color.*—Young upper and lower surfaces; 144B, mature upper surface; mostly 146A with a hue of 147A, mature lower surface; 146A.

*Leaf attachment.*—Sessile.

*Petioles.*—No petioles, leaves growing directly from the stem, sometimes growing underneath lateral branches.

Inflorescence description:

*Inflorescence type.*—Corymb.

*Inflorescence number.*—1 per stem.

*Inflorescence fragrance.*—None.

*Inflorescence size.*—Average of 34 cm in depth and 38 cm in diameter.

*Peduncles.*—Oval in shape, up to 4 cm in length and 2 mm in diameter, surface semi glossy, ridged and glabrous, color; inner side of peduncle is 187A, outer side of peduncle is 144A and sometimes a blend of 187A and 144A.

*Pedicels.*—Oval in shape and up to 3.5 cm in length and 1 mm in diameter, surface semi glossy, ridged and glabrous, color; inner side of peduncle is 187A, outer side of peduncle is 144A and sometimes a blend of 187A and 144A.

*Phyllaries.*—About 50 per capitulum, discoid head, acute tips, entire margins, bluntly acute base, smaller phyllaries linear in shape, up to 2 mm in length and 1 mm in width, color of outer and inner surfaces; tip is N92A, remaining surfaces 144A in color, larger phyllaries lanceolate in shape average of 8 mm in length and 2 mm in width, color of outer and inner surfaces; tip to mid section and margins a blend of 59A and 60B, mid section to base 196A.

*Floret buds.*—Linear in shape, average of 7 mm in length and 1 mm in width, color; base 155A, mid section a blend of N78A and NN74B, tip NN74A.

*Flower longevity.*—Average of 3 to 5 days, depending on temperature.

*Floret type.*—Discoid florets, no ray florets.

*Floret quantity.*—Average of 16 florets per capitulum.

*Floret.*—Just before floral anthesis; 1 cm in depth, 5 mm in width, elongated tube in shape and flat on top, base a blend of 146D and 146A, mid section a blend of N79A, 187A and 187B, tip is a blend of 186A and 61A and 64A, when open; average of 1.3 cm in diameter and 1.2 cm in depth, base 142B, mid section a blend of 59B and N79A, tip is a blend of 77A, N77A, N78A and 164C.

*Petals.*—5 petals, 50% of petals fused, free top portion; base to mid section is linear in shape, un-fused portion of petals drop into downward hanging angles and slightly curl under, tube is 6 mm in length and 1 mm in width, loose petals at top are 3 mm in length and 0.5 mm in width, petal tips acute in shape, inner and outer surfaces are translucent, glabrous and slightly velvety, entire margins, base fused to tube, color; inner and outer surfaces; base is 84C, mid section to tips are a blend of N82A, 83B and 83C.

*Pistils.*—1 per floret, bifid stigma, 2 mm in length and <0.5 mm in width, 83A in color, style 5 mm in length and <0.5 mm in width, 151A and translucent in color, ovary is 1 mm in length and width, 155B in color, pappus bristles at base, 7 mm in length, color ranging between 183A and N187A.

*Stamens.*—1 per floret, 4 filaments very fine, 5 mm in length, a blend of 83A and 155A in color, 2 anthers 3 mm in length, <0.5 mm in width, color when first blooming; NN155B, 83A at tip, color when aged; 165C to 165D, moderate amount of pollen observed when first blooming; NN155B in color.

*Fruit/seeds.*—Fruit and seed production was not observed to date.

It is claimed:

1. A new and distinct variety of *Vernonia* plant designated 'Summer's Swan Song' as described and illustrated herein.

* * * * *